(12) United States Patent
Stangenberg

(10) Patent No.: US 6,363,944 B1
(45) Date of Patent: Apr. 2, 2002

(54) DEVICE FOR THE REMOVAL OF CALLOUSES, ESPECIALLY DURING CHIROPODY

(75) Inventor: Wilfried Stangenberg, Remscheid (DE)

(73) Assignee: "Credo" Stahlwarenfabrik Gustav Kracht GmbH & Co. KG (DE)

( * ) Notice: Subject to any disclaimer, the term of this patent is extended or adjusted under 35 U.S.C. 154(b) by 0 days.

(21) Appl. No.: 09/494,269

(22) Filed: Jan. 31, 2000

(30) Foreign Application Priority Data

Jan. 29, 1999 (DE) .................................. 299 01 517 U

(51) Int. Cl.[7] .............................................. A45D 29/18
(52) U.S. Cl. ...................... 132/76.4; 132/75.4; 132/75.3
(58) Field of Search ........................... 132/76.4, 75.4, 132/75.5, 75.6; 30/527, 278, 26, 329, 330; 660/172, 167

(56) References Cited

U.S. PATENT DOCUMENTS

| | | | | | |
|---|---|---|---|---|---|
| 2,286,190 A | * | 6/1942 | Abrahamsen | ............... | 132/76.4 |
| 2,534,666 A | * | 12/1950 | Grisso | ....................... | 132/76.4 |
| 2,573,487 A | * | 10/1951 | Potvin | ....................... | 132/76.4 |
| 2,612,683 A | * | 10/1952 | Potvin | ....................... | 132/76.4 |
| D186,752 S | * | 11/1959 | Dean | .......................... | D86/10 |
| 3,600,803 A | * | 8/1971 | Nachsi | ....................... | 132/75 |
| 3,636,625 A | * | 1/1972 | Pracht | ......................... | 30/26 |
| 3,797,505 A | * | 3/1974 | Gilhaus et al. | ............ | 132/76.4 |
| 4,347,663 A | * | 9/1982 | Ullmo | .......................... | 30/47 |
| 5,601,584 A | * | 2/1997 | Obagi et al. | ................ | 606/172 |

* cited by examiner

*Primary Examiner*—Gene Mancene
*Assistant Examiner*—Robyn Kieu Doan
(74) *Attorney, Agent, or Firm*—R. W. Becker & Associates; R. W. Becker

(57) ABSTRACT

A device for removing callouses, especially in chiropody, is provided. A functional element is exchangeably arranged on a handle. To make mounting easy and safe, the functional element can be clamped between a front mounting segment of the handle and a fastening element that is articulated on the mounting segment. In a first position, the fastening element is pivotable about a pivot axis that runs perpendicular to the longitudinal direction of the handle. In a second position, the fastening element is displaceable relative to the handle via guides provided on the mounting segment. The fastening element can be fixed in a positive manner to the mounting segment by being displaced in the direction toward a rear handling segment of the handle.

14 Claims, 3 Drawing Sheets

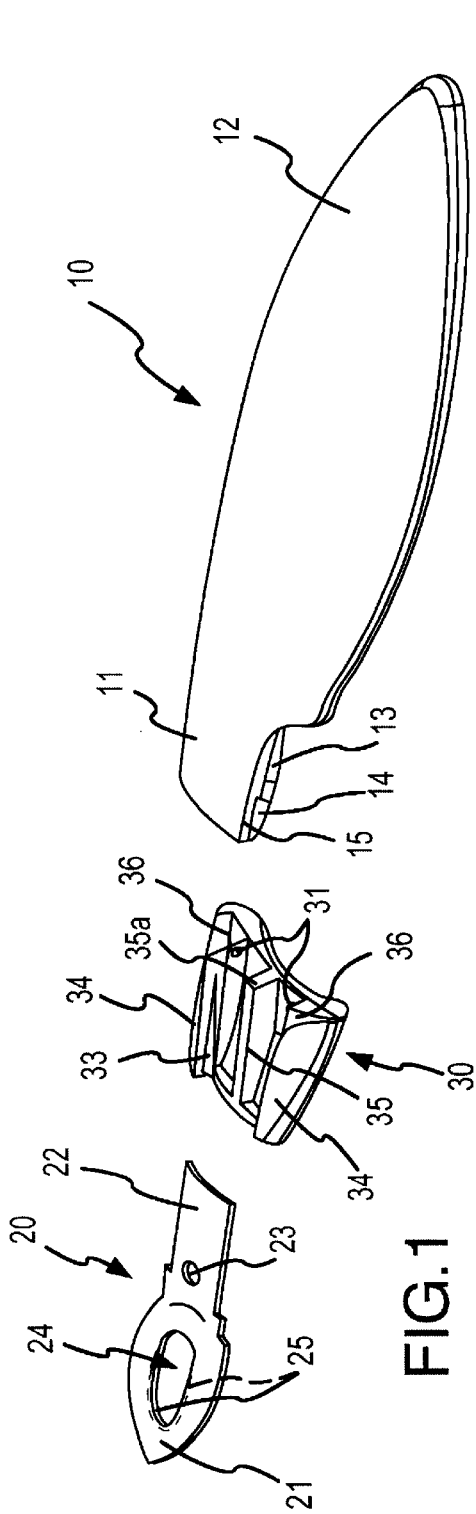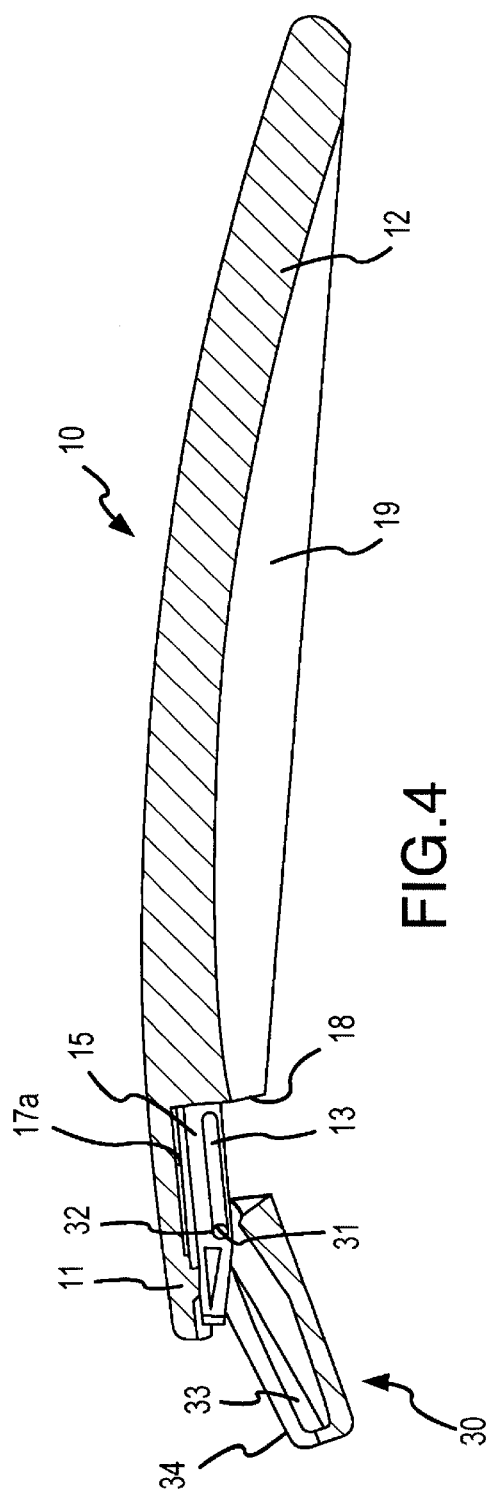

DEVICE FOR THE REMOVAL OF CALLOUSES, ESPECIALLY DURING CHIROPODY

BACKGROUND OF THE INVENTION

The invention relates to an apparatus for removing callouses, especially in chiropody, comprising a handle and a functional element exchangeably arranged thereon.

Various designs of such apparatus are known and are used especially in cosmetic care for removing dead and calloused epidermal cells, e.g. corns. Depending on the design of the functional element, these are primarily distinguished by callous files and callous planes that have teeth relatively distanced from each other compared to files and that generally have one or a plurality of razors. With regard to simple cleaning and the wear that is unavoidable over time, the functional element in the handle is generally arranged so that it can be exchanged.

Known callous planes have a mounting member for this purpose; an exchangeable razor blade can be mounted therein. It is disadvantageous that this entails unsatisfactory handling, which is caused by the fact that the razor, which is manually placed in the mount, is fixed in a locking connector, e.g. by a cover plate that is connected via a hinge to a receiving plate for the razor and that can be fixed to an end edge of the receiving plate in a type of snap connection. Although the razor is held in place in a positive and as a rule also in a frictional manner, there is insufficient protection against the risk of cuts on the sharp edges of the razors due to the fact that the cover plate must always be manually pressed onto the receiving plate.

The object of the invention is to further develop an apparatus for removing callouses such that exchanging the functional element is simple and safe.

SUMMARY OF THE INVENTION

This object is solved in an apparatus with the features cited in the foregoing in that the functional element can be clamped between a front mounting segment of the handle and a fastening element articulated thereon, whereby in a first position the fastening element is pivotable around a pivot or swivel axis that runs perpendicular to the longitudinal direction of the handle and in a second position it is displaceable relative to the handle via guides embodied on the mounting segment, and whereby the fastening element can be fixed in a positive manner to the mounting segment by being displaced in the direction of a rearward handling segment of the handle.

Such an apparatus facilitates more simple and safer exchanging of the functional element compared to the apparatus known in the prior art. The reason for this is primarily that the fastening element is both pivotable and displaceable on the mounting segment of the handle. This makes it possible to provide the fastening element with two positions that differ kinematically. In the first position, the fastening element is pivotable and, when it is in the swivelled position relative to the handle, also ensures simple and rapid placement of the functional element on the mounting segment. The guides embodied thereon help ensure that the fastening element in the second position is displaceable relative to the handle in a defined manner that permits the fastening element and the mounting segment to join in a positive manner, whereby the functional element is simultaneously mounted between mounting segment and fastening element. In contrast to the prior art, the apparatus in accordance with the invention thus has two different directions of movement for the fastening element for guiding or attaching the functional element, namely, swivel movement in the first position and linear movement in the second position. Furthermore, simple handling and safe holding of the fastening element to the mounting segment is provided during working motion in the longitudinal direction of the handle in that the fastening element is joined in a positive manner to the mounting segment by a linear displacement in the direction of a rearward handling segment in the handle.

Particularly advantageous is that the fastening element is provided with two pivots or pins that are guided for pivotable and displaceable bearing in oblong recesses in the mounting segment. This offers the advantage of a simple embodiment in terms of construction that permits cost-efficient production. Furthermore advantageous is that the pins at their free ends are provided with an incline for insertion into the oblong recesses so that the fastening element can be articulated to the mounting segment by placement thereon in a manner favorable for assembly.

In order to obtain reliable linear movement of the fastening element, in a further development of the invention it is suggested that the mounting segment have prism-shaped or dovetail-shaped guide cams that engage in corresponding guide channels in the fastening element for its linear displacement. It is useful that the guide cams and oblong recesses are embodied on the exterior side of the lateral walls of the mounting segment and preferably are arranged mutually offset in the direction perpendicular to the direction of displacement for the fastening element. The embodiment of the guide cams and recesses on the exterior side of side walls of the mounting segment ensures simple and rapid assembly, while the offset arrangement thereof contributes to a simple and rapid change from swivel movement to linear movement and vice versa.

In accordance with a further advantageous feature of the invention, each of the pins and guide channels is each arranged mutually opposing on the interior side of laterally standing walls of the fastening element and is provided between the walls with at least one preferably parallel ridge, the height of which is less than that of the walls, and by means of which the functional element can be mounted with the mounting segment. Such an embodiment ensures that the fastening element encompasses the lateral walls of the mounting segment, whereby the fastening element and mounting segment are mutually centered and fixed in the transverse direction. In order to join the fastening element and the mounting segment in a positive manner and in a structurally straightforward manner, furthermore suggested in a further development of the invention is to provide play between guide cams and guide channels that becomes increasingly smaller when the fastening element is displaced in the direction of the rearward handling segment, whereby preferably the cam followers and guide channels in the end position of the fastening element constitute a tight fit. The latter additionally ensures that the fastening element and the mounting segment remain reliably joined even during a working movement in the longitudinal direction of the handle.

In accordance with an advantageous further development of the invention, the mounting segment is embodied narrower and lower than the handling segment in order to form an end stopping surface for the fastening element. Providing an end stopping surface for the fastening element permits a higher tolerance for the design of the guides, especially the guide cams and guide channels, whereby economically favorable production overall can be achieved.

In order simply and safely to place the functional element onto the mounting segment and to mount it between the mounting segment and the fastening element, in accordance with another advantageous further development of the invention, the bottom of the mounting segment facing the fastening element is provided with a pin-shaped projection that, when the functional element is mounted, engages in a recess embodied therein, whereby the functional element is both centered and fixed with a positive fit. Advantageously on the bottom of the mounting segment, preferably on its lateral walls, receiving surfaces for the functional element are embodied that facilitate manual placement of the functional element and ensure secure frictional engagement.

In a preferred embodiment of the invention, the functional element is made of a functional part embodied essentially in a bowl-shaped depression and a fastening part that has a recess and that is arched in the transverse direction, whereby the functional part has an opening, the interior edge of which is provided with at least a partial cutting edge. In contrast to conventional razor blades, such a functional element has an inwardly disposed cutting edge, which substantially reduces the risk of injury during exchange. Furthermore advantageous is that the working field is easily visible through the hole in the functional part. The fastening part that is arched in the transverse direction furthermore ensures that the functional element is centered relative to the ridge of the fastening element that effects the mounting and that the functional element lies on the receiving surfaces of the mounting segment, whereby the functional element is reliably mounted in both the longitudinal and transverse directions.

In order to achieve gentle removal of the callous to be treated, in accordance with a further feature of the invention the opening of the functional part is embodied conically tapering in the direction opposing the handle and the interior edge in the region of the pieces running toward each other are sharpened to a cutting edge. Finally it is suggested to provide an ergonomically-shaped handle made of plastic and an integral functional element comprising metal in order to ensure appropriate practical handling and simple, cost-efficient production.

BRIEF DESCRIPTION OF THE DRAWINGS

Details and additional advantages of the subject of the invention result from the following description of a preferred exemplary embodiment.

FIG. 1 is an exploded view of the handle, functional element, and fastening element of an apparatus in accordance with the invention;

FIG. 3c is a cross-section along the line IIIc—IIIc in FIG. 3a;

FIG. 3d is a cross-section along the line IIId—IIId in FIG. 3a; and,

FIG. 4 is a cross-section through the handle and fastening element articulated thereon along the line IV—IV in FIG. 3a.

DESCRIPTION OF THE PREFERRED EMBODIMENTS

Figure 2:
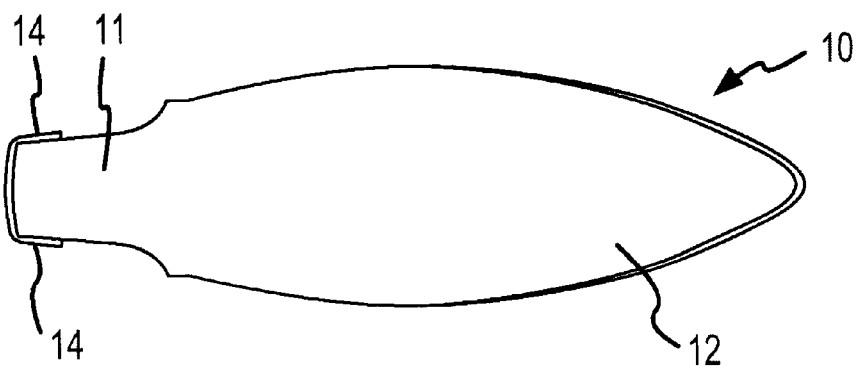
FIG. 2 is a top view of the handle.
Figure 2A:
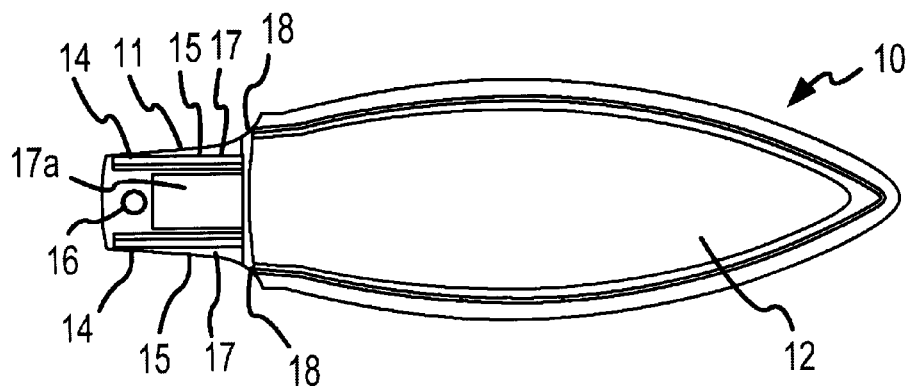
FIG. 2a is a view of the handle from below.
Figure 2B:
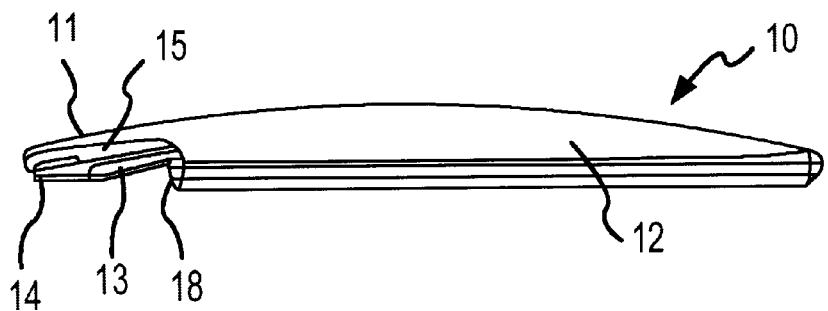
FIG. 2b is a side view of the handle.

FIG. 1 illustrates an apparatus for removing callouses in the form of a callous plane that has a handle 10, a functional element 20, and a fastening element 30. As can be seen particularly in FIGS. 2 through 2b and 4, the integral or one-piece handle 10 made of plastic comprises a front clamping or mounting segment 11 and an ergonomically shaped rearward handling segment 12, the bottom of which is embodied as an ergonomic, convex curvature 19 that is easy to grip and that is light-weight. Compared to the handling segment 12, the mounting segment 11 is narrower and lower, so that there is an end transversely slightly arched abutment or stopping surface 18 for the fastening element 30 in the transition region from the handling segment 12 to the mounting segment 11.

The mounting segment 11 on its bottom is provided with essentially parallel, downwardly projecting lateral walls 15, the exterior sides thereof that face away from each other each having an essentially wedge-shaped guide cam 14 and an oblong recess 13. As can be seen particularly in FIGS. 2b and 4, the guide cams 14 and the recess 13 are arranged mutually offset, both in the horizontal and vertical directions. Between the two lateral walls 15 on the bottom of the mounting segment 11 is arranged a pin-shaped projection 16 and a receiving surface 17a for the functional element 20. The receiving surface 17a is admitted into the bottom of the mounting segment 11 and is arranged offset in the vertical direction relative to receiving surfaces 17 embodied step-like on the bottom of the lateral walls 15.

The integral or one-piece element 20 made of metal and illustrated in FIG. 1 has a functional part 21 embodied as a bowl-shaped depression and furthermore has a fastening part 22 that is arched in the transverse direction. The functional part 21 is provided with an opening 24 that conically tapers in the direction opposing the handle 10. The interior edge of the opening 24, which runs essentially parallel to the exterior edge of the functional part 21, is sharpened to a nearly angular cutting edge 25 in the conical region. The fastening part 22 has a circular recess 23, the diameter of which is slightly greater than that of the pin-like projection 16. Depending on the configuration of the projection 16, the recess 23 can also alternatively be embodied in a polygon, i.e., to effect a positive fit.

Figure 3:
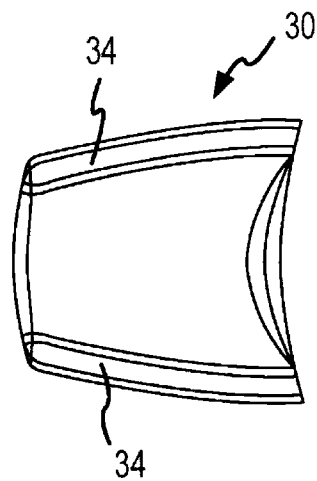
FIG. 3 is a view of the fastening element from below.
Figure 3A:
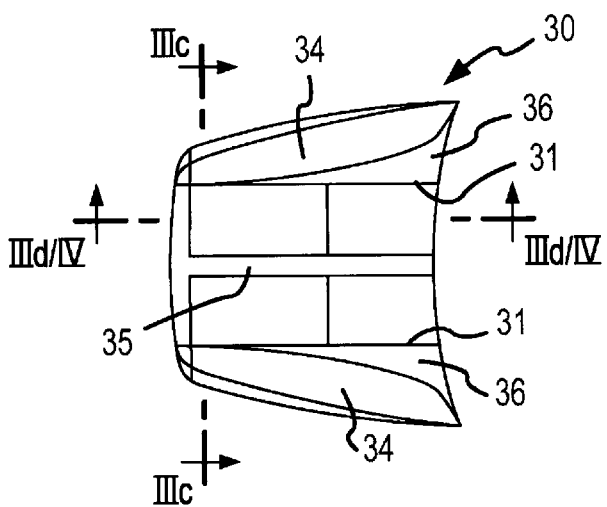
FIG. 3a is a top view of the fastening element.
Figure 3B:
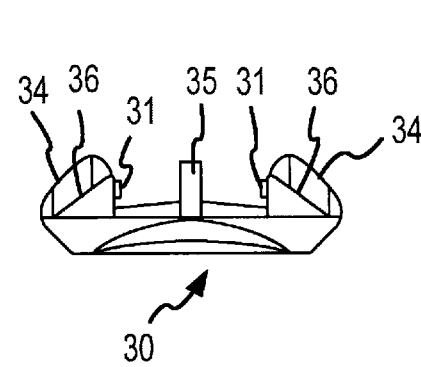
FIG. 3b is a side view of the fastening element on the side facing the handle in FIG. 1.
Figure 3C:
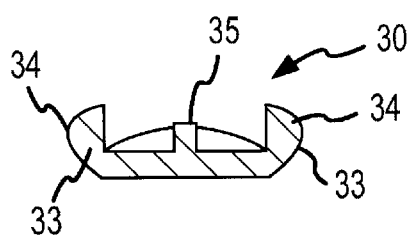
Figure 3D:
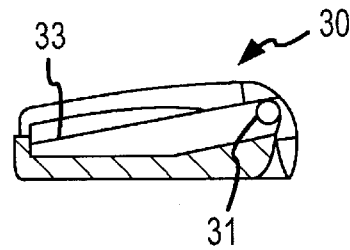

As can be seen especially from FIGS. 3 through 3d, the fastening element 30 has two lateral standing walls 34 that are embodied complementary to the lateral contour of the mounting segment 11 and when the fastening element 30 is fitted thereover, the handle 10 is enlarged in the region of the mounting segment 11. At each of the interior sides of the walls 34 facing each other are opposing pins 31 and guide channels 33. On their free ends the pins 31 are provided with an incline 32 that facilitates simple introduction of the pins 31 into the recesses 13. Arranged between the walls 34 is a ridge 35 running parallel thereto, the height of which increases from the end that faces away from the handle 10 to the opposing end of the fastening element 30, whereby the height is always less than that of the walls 34. Each of these is provided at the height of the guide channel 33 in the region of the pins 31 with an insertion surface 36 that is slightly arched transversely and that forms a stop. The distance between the guide channels 33 grows smaller in the direction of the end of the fastening element 30 facing away from the handle 10; consequently the play between guide cams 13 and guide channels 33 when the fastening element 30 is fitted thereon in the direction of the handling segment 12 likewise decreases and in this manner forms a tight fit in the end position of the fastening element 30, i.e., when the fastening element 30 is adjacent to the abutment surface 18, the mounting segment 11, and the fastening element 30.

It can be seen from FIG. 4 that the pins 31 engage in the recesses 13. The fastening element 30 is in this manner borne such that it can swivel with regard to the handle 10 and is furthermore borne displaceable in the recesses 13 in the longitudinal direction of the handle 10. If the fastening element 30 is swivelled into a position parallel to the handling segment 11, the bottom of the guide cams 14 rests against the insertion surface 36. When the fastening element 30 is subjected to linear displacement in the direction of the handling segment 12, the guide cams 14 engage in the guide channels 33 and constitute a prism-shaped guide, or, depending on the embodiment of the guide cams 14, even a dovetail-shaped guide, for the fastening element 30, which is fixed in a positive manner to the mounting segment 11 upon reaching the abutment surface 18, as described in the foregoing.

In order to mount or clamp the functional element 20 between the fastening element 30 and the mounting segment 11, the fastening part 22 is placed upon the receiving surface 17a made accessible by the fastening element 30 being swivelled relative to the handle 10. The projection 16 then engages in a positive fit in the recess 23, while the lateral edges of the slightly arched fastening part 22 are received by the receiving surfaces 17. When the fastening element 30 is swivelled into a position parallel to the mounting segment 11, the functional element 20 centered on the mounting segment 11 is secured against falling out by the top of the ridge 35. The subsequent linear movement of the fastening element 30, now guided by the guide cams 14 into the guide channels 33, causes the fastening part 22 to be clamped between the receiving surfaces 17, 17a of the mounting segment 11 and the top of the ridge 35. To avoid damage to the fastening part 22, the highest point of the ridge 35 when swivelled, the corner edge 35a that faces the handle 10, is rounded.

The callous plane described in the foregoing provides for simple and relatively safe exchange of the functional element 20. Contributing thereto are a fastening element 30 that is borne pivotable and displaceable on the mounting segment 11, the opening and closing mechanism associated therewith, and the functional part 21 embodied as a bowl-shaped depression with inwardly directed cutting edges 25. Finally, improved handling is also provided by the enlarged and expanded lateral walls 34 and the general ergonomic embodiment of the handle 10.

LEGEND

10 Handle
11 Mounting segment
12 Handling segment
13 Recess
14 Guide cams
15 Lateral wall
16 Projection
17 Receiving surface
17a Receiving surface
18 Stopping surface
19 Curvature
20 Functional element
21 Functional part
22 Fastening part
23 Recess
24 Opening
25 Cutting edges
30 Fastening element
31 Pins
32 incline
33 Guide channel
34 Wall
35 Ridge
35a Corner edge
36 Insertion surface

What is claimed is:

1. A device for removing callouses, comprising:

a handle having a front mounting segment and a rear handling segment;

a fastening element articulated on said mounting segment, wherein in a first position said fastening element is pivotable about a pivot axis that runs perpendicular to a longitudinal direction of said handle, and wherein in a second position said fastening element is displaceable relative to said handle via guide means provided on said mounting segment, wherein said guide means of said mounting segment include elongated recesses, wherein said fastening element is fixable in a positive manner to said mounting segment by being displaced in a direction toward said rear handling segment of said handle, wherein said fastening element is provided with two pins that are guided in said elongated recesses for a pivotable and displaceable mounting of said fastening element on said mounting segment, and wherein said guide means of said mounting segment also includes prism-shaped or dovetail-shaped guide cams that engage in corresponding guide channels provided in said fastening element for linear displacement thereof; and a functional element exchangeably clampable between said front mounting segment of said handle and said fastening element.

2. A device according to claim 1, wherein said pins have free ends that are provided with an incline to facilitate introduction into said elongated recesses.

3. A device according to claim 1, wherein said mounting segment is provided with sidewalls, and wherein said guide cams and said elongated recesses are disposed on outer sides of said sidewalls.

4. A device according to claim 3, wherein said guide cams and said elongated recesses are offset relative to one another in a direction perpendicular to a direction of displacement of said fastening element.

5. A device according to claim 3, wherein said fastening element is provided with lateral projecting walls, wherein said pins on the one hand and said guide channels on the other hand are respectively disposed opposite one another on inner sides of said walls, and wherein at least one preferably parallel ridge is disposed on said fastening element between said walls thereof, said at least one ridge having a height that is less than a height of said walls, wherein said functional element is adapted to be clamped with said mounting segment by means of said least one ridge.

6. A device according to claim 5, wherein play is provided between said guide cams and said guide channels, and wherein said play becomes increasingly less as said fastening element is displaced in a direction toward said rear handling segment.

7. A device according to claim 6, wherein in an end position of said fastening element said guide cams and said guide channels form a tight fit.

8. A device according to claim 1, wherein said mounting segment is narrower and lower than said rear handling segment to thereby form an end abutment surface for said fastening element.

9. A device according to claim 1, wherein an underside of said mounting segment that faces said fastening element is provided with a pin-shaped projection for engaging a recess of said functional element when said functional element is clamped between said mounting segment and said fastening element.

10. A device according to claim 3, wherein an underside of said mounting segment, is provided with receiving surfaces for said functional element.

11. A device according to claim 10, wherein at least some of said receiving surfaces are provided on said sidewalls of said mounting segment.

12. A device according to claim 1, wherein said functional element includes a functional part embodied essentially as a bowl-shaped depression, and also includes fastening part that has a recess and that is arched in a transverse direction, whereby said functional part is provided with an opening, an interior edge of which is at least partially provided with a cutting edge.

13. A device according to claim 12, wherein said opening of said functional part conically tapers in a direction away from said handle, and wherein said cutting edge is provided in the vicinity of said interior edge where said opening comes together, with such cutting edge being sharpened nearly angularly.

14. A device according to claim 12, wherein said handle is an ergonomically-shaped plastic handle, and wherein said functional element is a monolithic metal component.

* * * * *